United States Patent [19]

Hedlund et al.

[11] Patent Number: 5,268,165

[45] Date of Patent: Dec. 7, 1993

[54] POLYMER-DEFEROXAMINE-FERRIC IRON ADDUCTS FOR USE IN MAGNETIC RESONANCE IMAGING

[75] Inventors: Bo E. Hedlund, New Brighton; Philip E. Hallaway, Minneapolis, both of Minn.

[73] Assignee: Biomedical Frontiers, Inc., Minneapolis, Minn.

[21] Appl. No.: 926,906

[22] Filed: Aug. 7, 1992

Related U.S. Application Data

[63] Continuation of Ser. No. 598,044, Oct. 16, 1990, abandoned.

[51] Int. Cl.$^5$ .................... G01N 24/08; A61K 37/14; A61K 31/715
[52] U.S. Cl. .......................................... 424/9; 514/6; 514/54; 514/57; 514/59; 514/60; 514/836; 436/173; 436/806; 128/653.4
[58] Field of Search .................... 429/9; 514/6, 54, 57, 514/59, 60, 836; 436/173, 806; 128/653.4, 654

[56] References Cited

U.S. PATENT DOCUMENTS

| | | | |
|---|---|---|---|
| 3,471,476 | 10/1969 | Gaeumann et al. | 260/239.3 |
| 3,634,407 | 1/1972 | Gaeumann et al. | 260/239.3 |
| 4,024,073 | 5/1977 | Shimizu et al. | 252/315.3 |
| 4,419,365 | 12/1983 | McLachlin | 514/575 |
| 4,425,319 | 1/1984 | Yokoyama et al. | 424/1.1 |
| 4,530,963 | 7/1985 | Devoe et al. | 525/54.1 |
| 4,637,929 | 1/1987 | Quay | 424/9 |
| 4,647,447 | 3/1987 | Gries et al. | 424/19 |
| 4,719,098 | 1/1988 | Weinmann et al. | 424/9 |
| 4,822,594 | 4/1989 | Gibby | 424/9 |
| 4,863,964 | 9/1989 | Hedlund et al. | 514/575 |
| 4,909,257 | 3/1990 | Engelstad et al. | 128/654 |
| 4,915,933 | 4/1990 | Matwiyoff | 424/9 |
| 4,933,441 | 6/1990 | Gibby | 536/112 |
| 4,963,344 | 10/1990 | Gries et al. | 424/9 |
| 4,985,233 | 1/1991 | Klaveness et al. | 424/9 |
| 4,999,445 | 3/1991 | White et al. | 556/138 |

FOREIGN PATENT DOCUMENTS 0186947 7/1986 European Pat. Off. .
0243929 4/1987 European Pat. Off. .
59-215321 12/1984 Japan .

OTHER PUBLICATIONS

Abstract of German Patent Specification No. 1,186,076 (1989).
Fleming et al., Acta Biol. Med. Ger. 30:177–183 (1973). A copy of the German language document and an English abstract. Abstract only.
Gibby et al., Investig. Radiol. 25: 164–172 (1990).
Worah et al., Investig. Radiol. 23: S281–S285 (1988).
Weinmann et al., A.J.R. 142: 619–624 (1984).
Schmiedl et al., A.J.R. 147: 1263–1270 (1986).
Brasch et al., in Contrast and Contrast Agents in Magnetic Resonance Imaging, pp. 74–93, Special Topic Seminar, P. A. Rinck (ed.), European Workshop on Magnetic Resonance in Medicine, Belgium (1989).
Paajanen et al., Magn. Reson. in Med. 13: 18–43 (1990).
Gibby et al., Invest. Radiol. 24: 302–309 (1989).
Shreve, P., and A. M. Aisen, Magn. Reson. Med. 3: 336–340 (1986).
Hallaway et al., Proc. Natl. Acad. Sci (USA) 86: 10108–10112 (1989).
Wesbey et al., Physiol. Chem. Phys. and Med. NMR 16: 145–155 (1984).
Farber et al., Circ. Res. 63: 351–360 (1988).
Ramirez et al, J. Macromol. Sci. —Chem. A7: 1035–1045 (1973).
Ramirez et al, J. Macromol. Sci.—Chem. A10((1&2): 309–365 (1976).

(List continued on next page.)

Primary Examiner—Glennon H. Hollrah
Assistant Examiner—Gary E. Hollinden
Attorney, Agent, or Firm—Merchant, Gould, Smith, Edell, Welter & Schmidt

[57] ABSTRACT

Compositions comprising a covalently bounded adduct of deferoxamine, ferric iron and polymer for image enhancement in magnetic resonance (MR) imaging are provided. A pharmaceutical composition comprising the adduct and method of using the composition in magnetic resonance imaging are also disclosed.

10 Claims, 2 Drawing Sheets

OTHER PUBLICATIONS

Dawson et al., in "Development of Iron Chelators for Clinical Use," pp. 201-209, Martell, Anderson and Badman (eds.), Elsevier/North Holland (1981).

Brasch et al., *A.J.R.* 142: 625-630 (1984).

Kaplan et al., *Clinical Research* 34: 670A (1986).

Neidrach et al., Investig. Radiol. 23: 687-691 (1988).

Wilson et al., in *Immunofluorescence and Related Staining Techniques*, pp. 215-224, Knapp et al. (eds.), Elsevier/North Holland Biomedical Press (1978).

Tam et al., *Proc. Natl. Acad. Sci.* (USA), 73: 2128 (1976).

*Remington's Pharmaceutical Sciences* (16th ed.), pp. 759-761, A. Osol (ed), Mack Publishing (1980).

Niendorf, H. P. and J. Haustein, in *Contrast and Contrast Agents in Magnetic Resonance Imaging*, pp. 21-32, Proc. Europ. Workshop on Magnetic Resonance in Medicine (Sep. 1988).

Bolli et al., *Am. J. Physiol.* (Heart Circ. Physiol.) 22: H1372-H1380 (1987).

POLYMER-DEFEROXAMINE-FERRIC IRON ADDUCTS FOR USE IN MAGNETIC RESONANCE IMAGING

This is a continuation of application Ser. No. 07/598,044, filed Oct. 16, 1990, now abandoned.

FIELD OF THE INVENTION

The invention is directed to a composition for enhancing magnetic resonance (MR) imaging. The composition comprises a ferric iron-chelator complex bound to a polymer moiety. More particularly, the composition comprises an adduct of deferoxamine moieties, ferric iron and polymer which may be water-soluble, as for example, a protein or polysaccharide, or water-insoluble, as for example, a cellulose or agarose. The composition is capable of safely introducing large concentrations of ferric iron into the vascular system or gastrointestinal tract. The invention is further directed to a pharmaceutical composition and method of using the composition in MR imaging.

BACKGROUND OF THE INVENTION

Proton magnetic resonance imaging is a relatively new diagnostic technique in the field of medical imaging of the body's internal structure. Magnetic resonance (MR) images of the human body are obtained by exposing the protons, that is, hydrogen atom nuclei, contained in the water in tissue to the combined action of high magnetic fields and radio frequency waves. The MR image, derived from the MR signals, depends on the density of the protons in a given tissue, and on the two relaxation parameters of these protons which are referred to as T1 and T2.

In the human body, the most intense T1 signal is obtained from fatty tissue due to low concentrations of water whereas tissues containing high concentrations of water, as for example, cerebrospina fluid and edematous tissue, provide a T1 signal of low intensity. Compartments containing high concentrations of proteins, such as the blood stream and muscle tissue, are associated with an intermediate T1 signal intensity. The administration of a paramagnetic ion into a specific compartment will alter the T1 proton relaxation. The introduction of the magnetic field associated with one or more unpaired electrons will alter the interactions between the protons and their environment. As a result, the T1 relaxation time of the protons will be shortened. The magnitude of this change is dependent on the relative concentration of both protons and the paramagnetic ion.

Paramagnetic ions such as iron, manganese and gadolinium have been utilized as contrast enhancers. Of these ions, gadolinium, by virtue of its seven unpaired electrons, has the largest effect on the T1 value of protons. Accordingly, this ion has been utilized extensively to achieve contrast enhancement. Gadolinium does not occur in the human body and is associated with considerable toxicity when injected into animals as a salt solution, such as gadolinium chloride (Gibby, et al., *Investig. Radiol.* 25: 164–172 (1990)). To decrease the toxicity of gadolinium, the ion is normally administered in a complex form using organic chelators. Iron and manganese, although naturally occurring in biomolecules, are also intrinsically toxic ions. Their toxicity can also be reduced by chelation. In the case of iron, deferoxamine, has been employed to reduce toxicity (Worah, et al., *Investig. Radiol.* 23: S281–S285 (1988)).

Gadolinium has been detoxified by complexation with ethylenediaminetetraacetic acid (EDTA) and diethylenetriaminepentacetic acid (DTPA) (Weinmann, et al., *A.J.R.* 142: 619–624 (1984)). The Gd-DTPA chelate distributes within the extracellular fluid compartment, does not penetrate the blood-brain-barrier, and is rapidly eliminated by the kidney (Schmiedl, et al., *A.J.R.* 147:1263–1270 (1986)). Accordingly, Gd-DTPA is useful as a contrast agent for urographic imaging, for detecting abnormal capillary permeability from inflammation and tumors, and for assessment of the integrity of the blood-brain-barrier.

However, the use of Gd-DTPA as a contrast agent has limitations. Gd-DTPA is quickly eliminated from the intravascular compartment, about 50% being cleared from the vascular space into the extravascular fluid compartment on the initial pass through the capillaries (Schmiedl, et al., *A.J.R.* 147: 1263–1270 (1986)). As such, Gd-DTPA cannot provide selective enhancement of the intravascular space such that blood volume or tissue perfusion, for example, may be assessed.

To overcome such limitations and provide a contrast agent capable of intravascular retention, macromolecular components such as proteins and polysaccharides, as for example, albumin, cellulose and molecular weight dextrans having molecular weights of about greater than 50,000 have been attached covalently to DTPA with subsequent chelation to gadolinium (Brasch, et al., In *Contrast and Contrast Agents in Magnetic Resonance Imaging*, Special Topic Seminar, P. A. Rinck (ed.), European Workshop on Magnetic Resonance in Medicine, Belgium, pp. 74–93 (1989)). Protein-(Gd-DTPA) conjugates have been prepared with human and bovine serum albumin, immunoglobulin G, and fibrinogen. Such contrast agents have shown predominant intravascular distribution and retention (Schmiedl et al., *A.J.R.* 147: 1263–1270 (1986)); Paajanen, et al., *Magn. Reson. in Med.* 13: 18–43 (1990)).

It has been found that attaching Gd-DTPA to a serum albumin molecule improves proton relaxation per mole of $Gd^{+3}$ over that observed with Gd-DTPA used alone, due to the slower tumbling rates of the protein molecule. For example, an increase of relaxivity values of about 1.4-to 2.0-fold, of about 3-fold, and of 5- to 10-fold over plain Gd-DTPA have been reported (Paajanen, et al., *Magn. Reson. in Med.* 13: 18–43 (1990)). By contrast, Gd-DTPA polymeric dextrans are only slightly better than Gd-DTPA in relaxation effectiveness on a per Gd ion basis. With polymeric material, however, fewer moles of gadolinium are required to effectively enhance intravascular structures as compared with free Gd-DTPA. In vivo imaging studies have shown that the Gd-DTPA protein conjugate remains mainly in the vascular space for up to 90 minutes after IV injection in rats (Schmiedl, et al., *A.J.R.* 147: 1263–1270 (1986)).

The use of albumin-(Gd-DTPA) suffers from several drawbacks. Albumin-(Gd-DTPA) is synthesized by reaction of the cyclic anhydride of DTPA with albumin followed by the addition of an excess of $Gd+3$ ions. The DTPA groups are covalently linked to the amine moieties of albumin, and the $Gd+3$ ion is chelated in the DTPA ligand (Schmiedl, et al., *A.J.R.* 147: 1263–1270 (1986)). However, by using a bifunctional chelating agent such as DTPA anhydride, cross-linking of the albumin moiety is likely to occur. Furthermore, since one of the coordination sites on the chelator is altered by this process, the affinity of the gadolinium ion for the protein bound chelator is reduced.

Another drawback of albumin-(Gd-DTPA) conjugates is that the relatively low coupling efficiency of albumin with DTPA requires the injection of a high quantity of human serum albumin. Concern has been expressed regarding the high potential for immunogenic reactions associated with its modified protein matrix.

Dextrans have been cross-linked with DTPA via a polymerization process to form molecules from small particles of 17,000 MW to large insoluble particles. A typical process for cross-linking dextrans with DTPA utilizes the anhydride of DTPA to achieve ester cross-linking of DTPA to dextran (Gibby, et al., *Invest. Radiol.* 24: 302-309 (1989)). However, since the DTPA anhydride is a bifunctional cross-linking agent, this polymerization process can prove to be difficult and cumbersome. In addition, that method leads to poorly defined products with broad distribution of molecular weights. Further, the solubility of the resulting compound is much lower than that of the starting dextran component. Further, the replacement of two of the five carboxylic acid groups on DTPA with ester cross-links to the polysaccharides results in a significant decrease in affinity of the DTPA dextran conjugate for the bound metal ion. It has been proposed that hydroxyl groups from the polysaccharides may partially compensate for the loss of negative charge, but no data has been offered in support of this hypothesis. (Gibby, et al., *Investig. Radiol.* 24: 302-309 (1989)).

Attachment of Gd-DTPA to a protein such as albumin or a polysaccharide moiety represents a means for obtaining a contrast agent that distributes in the vascular compartment without specificity. A current focus in MR imaging is on binding paramagnetics to proteins to provide contrast agents which are tissue- or function-specific. For example, a protein-image contrast conjugate has been prepared by combining antibodies with Gd-DTPA. See for example, Shreve, P. and A. M. Aisen, Magn. Reson. Med. 3:336-340 (1986).

One advantage of using gadolinium as the paramagnetic nucleus is the higher relaxivity as compared to ferric iron. As such, a lower concentration of gadolinium need be administered in order to obtain signal enhancement. However, the loss of gadolinium from DTPA is a known occurrence especially in cases where the DTPA anhydride is utilized for polymer attachment. Further, the association constant, or affinity, of gadolinium to DTPA is relatively low at neutral pH and, more importantly, rapidly decreases when the pH is lowered. This characteristic is a significant problem with in vivo administration, particularly during ischemic insults which lead to acidosis and a localized drop in pH to as much as a full pH unit.

Such instability of chelates presents the threat of in vivo dissociation of the metal complex into the potentially toxic form while within the body. Therefore, it is vital that such contrast agents remain stable to ensure that the paramagnetic ion remains in a sequestered, nontoxic form within the body.

Contrast agents containing ferric iron have been used as an alternative to gadolinium. Like gadolinium, however, ferric iron, must be detoxified for internal administration such as by chelation with deferoxamine (desferrioxamine; DFO). The acute and chronic toxicity of deferoxamine is relatively high, potentially causing hypotension when administered intravenously. Ferrioxamine is a stable complex of ferric iron ($Fe^{+3}$) and deferoxamine, having a binding constant of about $10^{-30}$ (Hallaway, et al., *Proc. Natl. Acad. Sci.* (USA) 86: 10108-10112 (1989)). Ferrioxamine (FO) is excreted primarily in the urine which makes it especially useful as an enhancing agent for the urinary tract. Further, it provides identification of local blood-brain-barrier defects and assessment of renal excretory functions (Wesbey, et al., *Physiol. Chem. Phys. and Med. NMR* 16: 145-155 (1984); Weinman, et al., *A.J.R.* 142: 619-624 (1984)). Unlike Gd-DTPA which has a plasma half-life of about 20 minutes, FO clearance is biphasic, with an initial phase of about 128 minutes whereby about one-half of the dose is eliminated, followed by a prolonged elimination phase with a half-life of over 7 hours (Worah, et al., *Investig. Radiol.* 23: 5281-5285 (1988)).

However, the toxicity of ferrioxamine (FO) is similar to that of deferoxamine (Hallaway, et al., *Proc. Nat. Acad. Sci. USA* 86: 10108-10112 (1989)). Side effects from fast intravenous injection of either compound may lead to dramatic blood pressure drop. (Niedrach, et al., *Investig. Radiol.* 23: 687-691 (1988)). Accordingly, ferrioxamine as a paramagnetic contrast agent can be used only in very low concentrations and is limited to the urinary excreting system. Furthermore, the relaxivity of ferrioxamine at 20 MHz and at 37 degrees is 1.4 $s^{-1}$ $mM^{-1}$, which is a factor of 3 lower than Gd-DTPA. Accordingly, ferrioxamine must be injected at a 2-3 times higher dose than gadolinium-containing chelates to produce the same relaxation effects.

Contrast agents comprising para- or ferromagnetic agents bound to proteins such as immunoglobulins, monoclonal antibodies and blood-pool markers have been suggested for use as tumor-specific MR agents (Paajanen, et al., *Magn. Reson. Med.* 13: 38-43 (1990)). To achieve a high degree of incorporation of iron, the metal chelator was initially attached to polyamino acids such as polylysine, polyglutamic acids, or other organic polymers such as polyacrylic acid (Shreve, P. and A. M. Aisen, *Magn. Reson. Med.* 3: 336-340 (1986)). Although this process yielded adducts with a high degree of bound iron ions, the method has several drawbacks. In addition to being relatively cumbersome, the final conjugate products comprise profoundly altered antibodies in a structural sense having a decreased immunoreactivity of between about 60-70%. Therefore, what may be gained in signal appears lost in specificity. Furthermore, polyamino acids do not interact as specifically and with as high affinity as chelators such as deferoxamine. Of particular concern is that loosely bound iron may be associated with considerable toxicity since this form of non-sequestered iron can participate in reactions leading to formation of toxic oxygen- and lipid-derived radicals. Iron bound to deferoxamine, however, cannot participate in such reactions since all coordination sites are occupied.

Therefore, an object of the invention is to provide a macromolecular paramagnetic contrast agent composed of ferric iron for use in magnetic resonance imaging that will enhance proton relaxation times, be free of toxic effects in doses appropriate for contrast enhancement in vivo, remain stable in vivo, retain and/or increase its biological half-life in vivo, and be quickly eliminated from the body after completion of the desired imaging study. Another object is to provide a ferric iron contrast agent which is capable of tissue-specific or compartment-specific distribution in a mammal. Yet another object is to provide a pharmaceutical composition comprising the paramagnetic adduct of the invention and a method of using the composition to enhance magnetic resonance imaging.

SUMMARY OF THE INVENTION

These and other goals are met by the present invention which is directed to a composition useful in magnetic resonance (MR) imaging. More particularly, the invention is directed to compositions which comprise an adduct of a conjugate of deferoxamine moieties covalently bonded to a polymer, and ferric iron chelated to the deferoxamine moieties. The polymer moiety according to the invention may be any macromolecular substance which is capable of decreasing the toxicity of the bound chelate component of the adduct. For example, the adducts may comprise water-soluble polymers such as polysaccharides, as for example, dextrans, starches, hyaluronic acid, inulin and celluloses, and proteins such as serum albumin and transferrin, or water-insoluble polymers such as celluloses, agaroses, and the like.

The contrast agent, or adduct, is formed by saturating the binding sites on polymer-bound iron chelators with iron. The deferoxamine moiety substantially retains its chelating ability after attachment to the polymer component. The resulting polymer-(chelator-ferric iron) adducts are non-toxic and provide for the introduction of high concentrations of bound, non-toxic, ferric iron into the vascular system, or compartment, or gastrointestinal tract of a mammal. Concentrations greater than 1 mM of ferric iron may be introduced into the bloodstream without harmful side effects. The adduct of the invention is capable of increasing the amount of ferric iron in the vascular compartment to about 5mM. Preferably, the amount of ferric iron in the vascular system provided by the adduct is about 0.5-2 mM. The ferric iron itself enhances the proton magnetic resonance signal. The magnetic signal is enhanced further by attaching the iron/chelator complex to the polymer.

The invention provides a composition suitable for in vivo administration for use in magnetic resonance imaging of a body feature of a patient. The pharmaceutical composition according to the invention comprises a pharmaceutically-acceptable adduct in combination with a biocompatible, pharmaceutically-acceptable carrier. It is preferred that the adduct is present in an amount effective to enhance the body feature being imaged.

The compositions of the invention are capable of selective magnetic resonance image enhancement of particular cells, tissues, and other features, particularly of the vascular system. The adducts of the invention are useful in MR imaging to monitor circulatory insufficiency, tumor infiltration, vascular leak, or edema, and tissue injured by ischemia and reperfusion. The invention includes MR image contrast agents with specificity for particular cells or tissues which are useful diagnostic tool, as for example, in cancer detection. For example, it has been demonstrated that various neoplastic cell types, including both vascular tumors, and solid tumors such as carcinoma of the breast, are associated with increased expression of the transferrin receptor. Accordingly, transferrin, an iron transporting protein, may be used as the polymer component of the adduct to enhance the distribution of such transferrin conjugates to cells and/or domains where the expression of binding sites, or receptors, for this protein are high.

The adducts provide for intravascular retention for the period of time required to provide effective contrast enhancement of the body feature being imaged, preferably 30-90 minutes. Preferably, the size of the adducts of the invention is effective to slow the rate of diffusion of the adduct from the vascular space into the extracellular fluid space so that the MR imaging of an organ, tissue or other feature of the vascular compartment can be achieved. The adduct is preferably at least about 5,000 Daltons and less than 250,000 Daltons, more preferably about 10,000 to 50,000 Daltons. After the imaging process is completed, the adduct is rapidly eliminated from the body, preferably within 24 hours. It is preferred that the adduct is eliminated from the body through the urinary system.

A method of using the composition comprising the adduct in MR imaging is also provided. The method comprises the steps of administering a composition composed of a contrast agent comprising a pharmaceutically-acceptable adduct according to the invention, such that the contrast agent is distributed to the body system being imaged, and determining the image of the system or a portion thereof according to an MR imaging technique.

DETAILED DESCRIPTION

Figure 1:
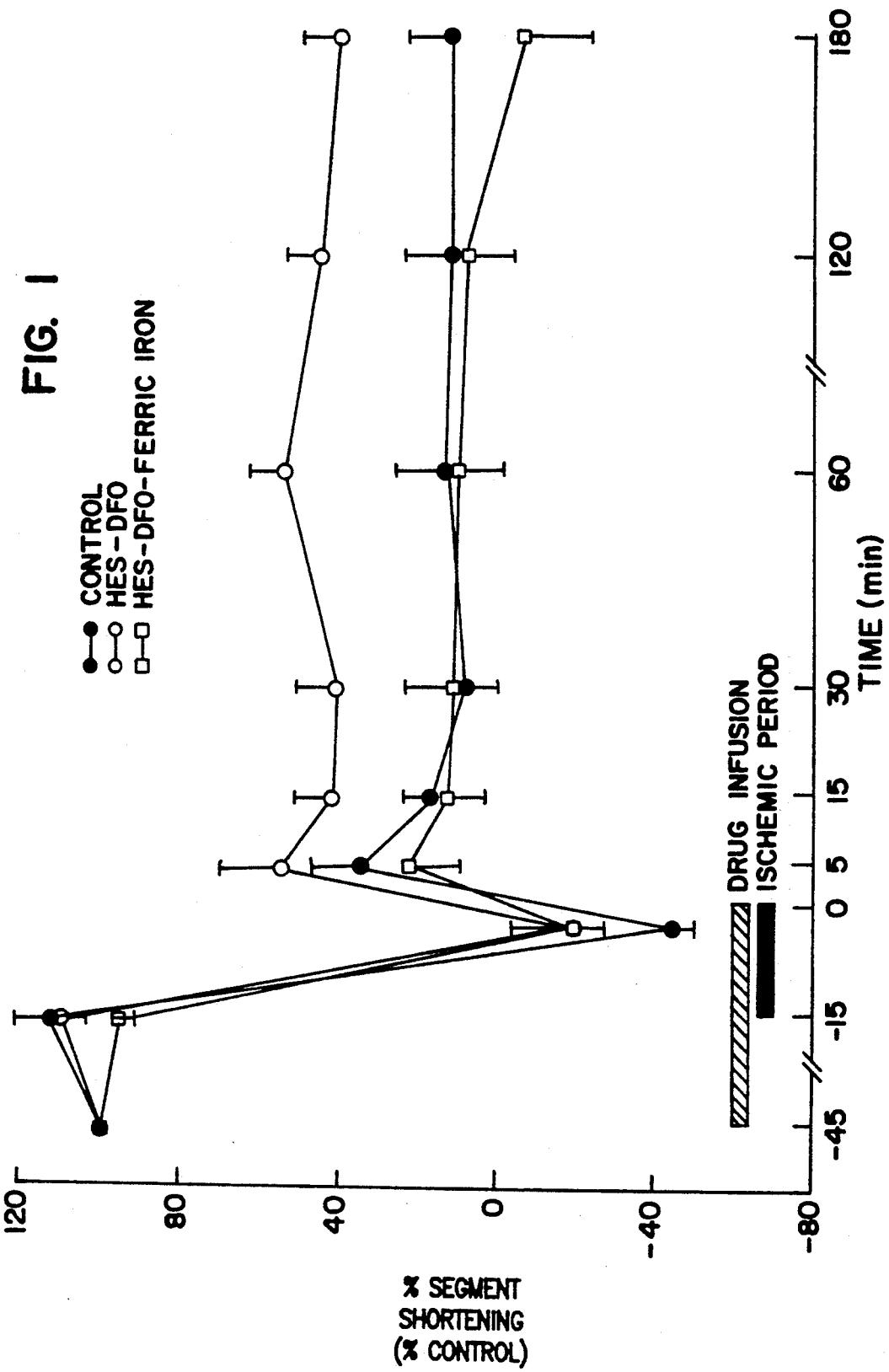
FIG. 1 illustrates the percent segment shortening of the ischemic-reperfused area (% of control) in the saline group (Control, closed circles, n=9), HES-DFO-treated group (open circles, n=7) and HES-DFO-FERRIC IRON-treated group (open squares, n=5) prior to left anterior descending coronary artery (LAD) occlusion, during occlusion and at various times following reperfusion. The hatched and closed bars indicate the period of drug infusion and LAD occlusion, respectively. All values are the mean ±SEM. * $p<0.05$ vs control group.

The present invention is directed to magnetic resonance (MR) imaging of a mammal using an MR contrast agent which is an adduct of a ferric iron-chelator complex covalently bound to a polymer component. In particular, it provides for enhancing the contrast of an MR image of the vascular compartment, that is, body features which are highly vascularized, as for example, the kidney, liver, heart, brain, and gastrointestinal tract. The invention provides improved MR contrast agents which may be produced by saturating the binding sites on polymer-bound chelators, particularly deferoxamine, with iron. The resulting compounds are non-toxic and provide for the introduction of high concentrations of bound, or sequestered, and thus non-toxic, ferric iron into body structures and systems, particularly the vascular system. The paramagnetic nature of ferric iron alone provides significant enhancement of the proton magnetic resonance signal by shortening the T1 relaxation time of protons. Additional enhancement of the magnetic signal is achieved by attaching a deferoxamine-ferric iron complex, or ferrioxamine, to a polymer component such as a protein or polysaccharide. Intravenous infusion of polymer-bound ferrioxamine provides a means for safely obtaining transient vascular concentrations of ferric iron at concentrations in excess of 1 mM. The composition of the invention further provides a means for selective magnetic resonance image enhancement of particular sites within the vascular system.

The polymer moiety may be any macromolecular substance which may decrease the toxicity of the bound chelate component. Suitable polymers according to the invention include water-soluble polymers such as polysaccharides, as for example, dextrans, starches, hyaluronic acid, inulin and celluloses, and proteins such as serum albumin and transferrin, and water-insoluble polymers such as celluloses and agaroses. Polymers may be designed to provide an adduct for a particular clinical need with respect to particular physiological distribution and vascular retention within a body. For example, the water-insoluble polymers provide adducts for gastrointestinal tract imaging while the water-soluble polymers provide adducts for vascular imaging.

The adduct of the invention should be of a size effective to deter rapid diffusion of the adduct from the intravascular to the extracellular fluid space, such that the adduct is retained intravascularly to provide effective contrast enhancement of the organ or tissue being imaged. It is preferred that the adduct is retained within the vascular compartment for about 30-90 minutes. Preferably, the adduct has a molecular weight, as determined by gel permeation chromatography, of between 5,000 to 250,000 Daltons, more preferably about 10,000 to 50,000 Daltons.

To prepare the adducts of the invention, the deferoxamine moiety is covalently bonded directly to a pharmaceutically-acceptable organic polymer and the conjugate is then saturated with ferric iron. Alternatively, the deferoxamine-ferric iron complex in a prepared form, as for example, ferrioxamine B, may be bonded to the polymer moiety, and the conjugate saturated with ferric iron. Methods for the preparation of deferoxamine (N-[5-[3-[(5-aminopentyl)hydroxycarbamoyl]propionamido]pentyl]-3-[[5-(N-hydroxyacetamido) pentyl]carbamoyl]propionohydroxamic acid) and its pharmaceutically-acceptable salts have been disclosed, e.g., by Prelog, et al., in *Helv. Chim. Acta*, 45: 631 (1962); Bickel, et al., *Helv. Chim. Acta*, 46: 1385 (1964); in German Pat. Spec. 1,186,076 and in U.S. Pat. No. 4,419,365, the disclosures of which are incorporated by reference herein. Such salts include the acid addition salts of methane sulfonic acid, phosphoric acid, acetic acid, lactic acid, tartaric acid, citric acid and the like.

It is preferred that the terminal amino (NH$_2$) group of deferoxamine is bound to a molecule of a pharmaceutically-acceptable organic polymer. The amino group may be bonded directly to a carboxy-acid moiety on the polymer, e.g., to form an amide linkage. Preferably, the deferoxamine amino group will be directly bonded to an aldehyde (CHO) moiety on the polymer via the reaction sequence:

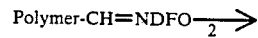

Polymer-CH$_2$NH—DFO wherein reaction 1 yields a Schiff base which is reduced in reaction 2 to yield a covalent linkage. Many deferoxamine moieties may be bound to a single polymer molecule.

Application of the above process, wherein the polymer is a soluble biopolymer such as a polysaccharide or a protein, leads to a soluble chelating agent which retains essentially the same chelating ability as the non-anchored chelate.

Aldehydic groups can be introduced into the polymer substrates by known techniques, e.g., by the oxidation of carbohydrates or other diols to dialdehydes with sodium metaperiodate. See, for example, Wilson, et al., in *Immunofluorescence and Related Staining Techniques*, Knapp, et al. (eds.) Elsevier/North Holland Biomedical Press (1978) at page 215; Fleming, et al., *Acta Biol. Med. Ger.* 30: 177 (1973); and, S.-C. Tam, et al., in *Proc. Natl. Acad. Sci.* (USA), 73: 2128 (1976), the disclosures of which are incorporated by reference herein.

In some applications, the terminal amino group on deferoxamine can also be bonded to an amino group on the polymer indirectly, by the use of a dialdehyde linking agent such as glutaraldehyde, followed by reduction, e.g., with sodium borohydride.

The mole ratios of deferoxamine:polymer attainable by these reactions will vary widely, depending on factors such as the number of reactive groups on the polymer, steric hindrance, rate and extent of Schiff base or amide formation, and the like. As an example, about 0.6-0.7 g of deferoxamine can be bonded to about 2.5 g of reacted Dextran 40, via reaction of the deferoxamine with aldehyde groups introduced into the dextran, followed by reduction. Organic polymers used as a substrate material for reaction with deferoxamine may be either water-soluble or water-insoluble. Chelating agents formed from either will have utility in various applications, provided the polymer and chelating agent are pharmaceutically- and/or otherwise compatible with the physiological solutions with which they will have contact during use.

In contrast to in vitro preparations, in vivo use of the adducts of the invention requires compositions having special characteristics. For example, the chelating moiety of the agent must remain effective as a chelator after attachment to the polymer. Preferably, the deferoxamine moiety is anchored to the polymer moiety in such a manner that the chelating ability of the deferoxamine moiety in vitro remains substantial, preferably the order of non-anchored deferoxamine. The adduct should be sufficiently soluble for ease of introduction and should provide increased retention in the vascular compartment compared to ferrioxamine alone. The adduct should be substantially non-toxic even when administered at concentrations 3 to 10 times higher than necessary for optimal contrast enhancement. The polymeric substrate should not cause significant side reactions, and thus should be selected from polymers which are biocompatible.

It has been found that polymers apparently useful for application according to an in vivo application of the present invention include polysaccharides such as the dextrans and hyaluronic acid, starch derivatives, and proteins such as serum albumin, transferrin and the like. Polymer starting materials such as the dextrans, hydroxyethyl starch, human albumin and plasma protein fraction are commercially available. See *Remington's Pharmaceutical Sciences*, A. Osol., ed., Mack Publishing (16th ed. 1980) at pages 759–761, the disclosures of which are incorporated by reference herein. Further, a wide variety of insoluble synthetic and natural organic polymers can be bound to deferoxamine by the techniques described hereinabove, including water-insoluble agaroses (Sepharose ®), cross-linked dextrans (Sephadex ®), cellulosics (e.g., paper and cotton), starches and the like.

Attachment of ferric iron to the deferoxamine-polymer conjugate can be accomplished by careful measurement of the content of bound deferoxamine, followed by the addition of 0.94–0.96 equivalents of ferric iron using ferric chloride. The pH of the solution is then adjusted to neutrality using sodium hydroxide.

Preferably, the ratio of deferoxamine to ferric iron in the adduct is about 1.2 to 1.01, most preferably 1.06 to 1.04. It is essential that a slight excess of deferoxamine is used in order to reduce and/or eliminate the occurrence of non-specifically bound iron which may be potentially toxic to the living system. A preferred embodiment of the composition according to the invention comprises about 3–40 wt-% deferoxamine, more preferably about 10–25 wt-%, about 0.3–4 wt-% ferric iron, more preferably about 1.0–2.5 wt-%. These synthetic iron chelator-polymer conjugates therefore contain a higher level of bound iron than transferrin, an iron transporting protein which, in its saturated form, contains approximately 0.15% of iron by weight.

The adduct of the invention exhibits substantial advantages, primarily relating to diminished toxicity of the deferoxamine-ferric iron moiety, and increased vascular retention time of the anchored deferoxamine-ferric iron moiety relative to non-anchored ferrioxamine. It will be understood from the below reported experimental results that behavior of the polymer bound deferoxamine-ferric iron adduct is not readily predictable from other polymer-bound MR contrast agents.

The polymer-(deferoxamine-ferric iron) adduct is capable of MR contrast enhancement in a mammal particularly of the vascular compartment, or, as in the case of oral administration, the gastro-intestinal system. For example, the adduct may enable MR detection of reperfusion of blood to damaged tissue upon restoration of arterial flow, enhance vascular tissues associated with the brain, or define tumors. Further, the adduct may enable the definition or detection by MR of hemorrhage sites such as a stroke, gradations in blood volume, extent of vascularity, or renal, intestinal, myocardial, or cerebral ischemia within minutes of onset. For example, deferoxamine-ferric iron complex conjugated to hydroxyethyl starch may be used to enhance the MR imaging of myocardial and brain blood vessels related to micro- and macrocirculation. Such an agent is useful in the diagnosis of vascular lesions of several types in a variety of organs. Further, the composition of the invention may enhance tissues in multiple anatomic regions without reinjection.

The MR contrast composition of the invention provides for intravascular retention effective to accomplish MR imaging of a particular organ or tissue. It is preferred that the adduct has a vascular half-life of at least about 30–90 minutes. For example, a 20,000 molecular weight hydroxyethyl starch-deferoxamine adduct according to the invention may be retained within the vascular compartment for 2 to 3 hours. After completion of the imaging procedure, it is preferred that the adduct is eliminated from the body. Preferably, the adduct is completely eliminated within 24 hours post-administration of the magnetic resonance imaging procedure. It is further preferred that the adduct is eliminated through the urinary system.

The adduct may also provide enhancement of other than the vascular compartment. For example, the adduct may be administered such as by injection, into the spinal cord to enhance structural details of cerebrospinal fluid circulation, the sinuses, the genito-urinary system, the lymphatic system, and any other systems which may be detected by MR procedures. For example, the adduct may provide enhancement of the lymphatic system by injection into lymph nodes such as the submandibular nodes, pre- and post-auricular nodes, superficial cervical nodes, axillary nodes, inguinal nodes, and the like. As further example, the adduct may be injected into the synovial fluid of a joint, for example, a race horse, for image enhancement of the ligaments and other structures.

The invention includes MR image contrast agents with specificity for particular cells or tissues which are useful as diagnostic tools, as for example, in cancer detection. Increased expression of transferrin receptors is a hallmark for a variety of neoplastic cell types, including both vascular tumors, and solid tumors such as carcinoma of the breast. Accordingly, the adduct of the invention may incorporate transferrin, an iron transporting protein, to augment the distribution of contrast agent conjugates to cells and/or domains where the expression of binding sites, or receptors, for transferrin are high. As such, MR image contrast agents which possess a specificity for cells with increased expression of the transferrin receptor thus provide a means for the diagnosis of cancerous cells and/or tissues.

The invention further includes a pharmaceutically-acceptable adduct of deferoxamine, ferric iron and polymer for administration to a mammal. The adduct of the invention may be combined with a pharmaceutically-acceptable vehicle such as a liquid or a powdered carrier, which is compatible with the adduct. For example, the adduct may be combined with hyaluronic acid for injection into the synovial fluid of the joint. The pharmaceutical composition may be formulated as a powder, granules, solution, ointment, cream, aerosol, powder, or drops. The solution or drops may contain appropriate adjuvants, buffers, preservatives and salts. The powder or granular forms of the composition may be combined with a solution and with diluting, dispersing and/or surface active agents. The composition may be administered orally, rectally, intravenously, parenterally, or by direct injection into the system being imaged.

The composition of the invention is preferably administered in vivo as a solution, parenterally, e.g., by intramuscular or intravenous injection or infusion, or via oral, rectal or vaginal routes. The composition may also be administered by direct injection into the system being imaged. The appropriate dose will be adjusted in accord with appropriate clinical factors including the organ or tissue to be enhanced, the patient's age, size and weight, the mode of administration, and the like.

The optimal dose of a particular contrast agent is dependent on a number of factors, such as the rate of excretion of the adduct, the relaxivity of the adduct, or whether the adduct becomes distributed within the extracellular environment. Where the agent remains in the vascular compartment, lower doses are needed.

However, the actual optimal dose will be dependent on any particular set of circumstances. It is preferred that the adduct is administered in an amount effective to enhance the resonance imaging of the organ being studied. Preferably, the dose of the polymer-(deferoxamine-ferric iron) conjugate is between about 0.01 and 0.1 millimoles/kg body weight, or about 6 to 60 mg/kg body weight ferrioxamine. Formulations of polysaccharide-deferoxamine-ferric iron adducts preferably contain about 5-20 mg/ml of immobilized deferoxamine-ferric iron complex. Preferably between 0.5 to 6 ml/kg body weight deferoxamine-ferric iron, more preferably about 1 ml/kg body weight, is administered. For oral administration of the adduct for enhancement of the gastrointestinal tract, larger volumes may be administered.

The invention further includes a method for magnetic resonance imaging of the body of a mammal. The method includes the steps of administering the composition containing the adduct of the invention to a patient such that the adduct is distributed to the body system being imaged, and determining the image of the body system or a portion thereof according to MR imaging techniques. See, for example, Niendorf & Haustein, In *Contrast and Contrast Agents in Magnetic Resonance Imaging;* Proc. Europ. Workshop on Magn. Reson. in Medic. (September 1988), the disclosure of which is incorporated by reference herein. The composition which is administered according to the method of the invention comprises a pharmaceutically-acceptable adduct of deferoxamine, ferric iron, and polymer in combination with a pharmaceutically-acceptable carrier. It is preferred that the adduct is present in an amount effective to enhance a magnetic resonance image of the body system being imaged. The method of the invention particularly provides for contrast enhancement of highly vascularized tissues in a mammal, although other systems such as the lymph system or the renal/urinary tract may also be enhanced according to the invention. To provide enhancement of the vascular system, it is preferred that the adduct is induced into the bloodstream. The composition may be administered orally, rectally, intravenously, parenterally, or by direct injection into the system being imaged.

An advantage of ferrioxamine-based adducts is the much higher affinity or binding constant of deferoxamine for ferric iron compared with that of DTPA for gadolinium ion. Accordingly, the adducts of the present invention will not degrade over the time required for the imaging study. The loss of Gd from DTPA is a known occurrence especially in cases where the DTPA anhydride is utilized for polymer attachment. The very high binding constant of ferric iron to deferoxamine ensures that the iron will not dissociate from the complex in vivo.

Another advantage of the polysaccharide-deferoxamine conjugates of the present invention is that both water-soluble and water insoluble conjugates can be prepared. Attachment of DFO to biocompatible, water soluble polysaccharides and proteins provides adducts which are well suited for parenteral injection. Attachment of the chelator-iron complex to insoluble matrices, such as celluloses, agaroses, and the like, provide adducts which are well suited for oral or rectal administration.

Yet another advantage of the present invention is that since the amino group of the chelator is used for attachment to the polymer, there is no risk of polymer cross-linking. As a result, the conjugates of the invention remain very similar in character to the starting polymer component. In contrast, attachment of DTPA anhydride, a bifunctional cross-linking agent, to polymers is associated with polymer-polymer cross-linking, which leads to large complexes with poorly defined molecular weight.

Another advantage is that the attachment of deferoxamine to the polymer moiety, according to the invention, does not alter the iron binding properties of the chelator. See Hallaway, et al., *Proc. Nat. Acad. Sci. USA* 86: 10108-10112 (1989), the disclosures of which are incorporated by reference herein.

Yet another advantage is that the polymer moiety of the invention are pharmaceutically-acceptable components. For example, hydroxyethyl starch, dextran, inulin and hyaluronic acid are used extensively in clinical treatment as plasma volume expanders.

A further advantage of the invention is that, unlike gadolinium conjugates, the ferrioxamine-containing compounds of the invention range in color from dark brown to orange and thus provide for enhanced visual detection of urinary excretion of the MR enhancing agent.

Due to the non-toxicity, increased biological half-life, and selectivity into the vascular compartment, the adducts of the invention provide improved contrast agents for enhancement of various organs and tissues in MR imaging as compared to agents such as free Gd-DTPA, Gd-DTPA conjugates, or free deferoxamine-ferric iron complex.

The invention will be described with reference to various specific and preferred embodiments and techniques. However, it should be understood that many variations and modifications may be made while remaining within the spirit and scope of the invention.

EXAMPLE I

Synthesis of an Adduct Comprising Hydroxyethyl Starch, Deferoxamine and Ferric Iron This example describes attachment of deferoxamine (DFO) to the polysaccharide hydroxyethyl starch (HES) and saturation of the conjugate with ferric iron to synthesize a high molecular weight polysaccharide-deferoxamine-ferric iron adduct.

Preparation of the Hydroxyethyl Starch-Deferoxamine Conjugate

Hydroxyethyl starch (HES) (Hetastarch, Dupont Critical Care, Waukegan, Ill.) was dissolved in water at a concentration of 100 grams per liter. Cleavage of cis-diols to yield reactive aldehyde groups was accomplished by addition of solid sodium metaperiodate to a final concentration of 100 mM. The solution was incubated for one hour at room temperature. Low molecular weight reaction products were removed from the mixture by diafiltration (Pellicon system, Millipore Corporation, Bedford, Mass.) with depyrogenated water using a 100,000 molecular weight cut-off filter (Millipore Corporation). The polymer concentration was adjusted to 100 grams/liter based on refractive index of the solution.

Deferoxamine was added as the mesylate salt to a final concentration of 100 mM and allowed to fully dissolve at room temperature. The resulting Schiff bases between the amino group of the deferoxamine and the aldehyde groups on the polymer were reduced by addition of sodium cyanoborohydride to a final concentration of 100 mM. After one hour at room temperature, sodium borohydride was added to a final concentration of 100 mM to reduce any residual aldehyde groups. The reaction mixture was gently stirred for 16 hours at room temperature.

Concentration of the polymer-deferoxamine conjugate and removal of low molecular weight contaminants were accomplished by thorough diafiltration, using a 30,000 molecular weight cut-off filter and pyrogen-free water. The concentration of the polymer-deferoxamine conjugate was adjusted to 130 grams/liter based on refractive index.

Saturation of the HES-DFO Conjugate with Ferric Iron

An aliquot of the HES-deferoxamine conjugate solution was removed, and the deferoxamine concentration was measured spectrophotometrically at 429 nm after the addition of excess ferrous sulfate. Conversion of the polymer-deferoxamine adduct to the iron-saturated polymer-deferoxamine-ferric iron form was accomplished by 94–96% titration of the deferoxamine with ferric chloride. A volume of ferric chloride stock solution (300 mM) was added to the polymer-deferoxamine solution while stirring. Following addition of ferric chloride, 1M sodium hydroxide was slowly added until the pH reached neutrality. The material was filtered through a 0.2 micron filter and transferred to sterile plastic bags.

The molecular weight distribution of the hydroxyethyl starch-deferoxamine-ferric iron adduct was determined by high pressure liquid chromatography and was unchanged from the distribution of the hydroxyethyl starch-deferoxamine conjugate.

The same procedure may be used to synthesize adducts comprising inulin, hyaluronic acid or dextran as the polymer moiety. In the case of inulin, which is relatively insoluble in its native form, the inulin-deferoxamine conjugate becomes more soluble following attachment of chelator.

EXAMPLE II

Synthesis of an Adduct Comprising Transferrin, Deferoxamine and Ferric Iron

This example describes attachment of deferoxamine to the protein transferrin, and saturation of the conjugate with ferric iron to form a high molecular weight protein-deferoxamine-ferric iron adduct.

Deferoxamine was attached to transferrin by glutaralehyde cross-linking. Initially, the deferoxamine-glutaraldehyde conjugate was prepared by slowly adding a 100 mM solution of deferoxamine into a 100 mM solution of glutaraldehyde with stirring. The resulting solution primarily contained the deferoxamine-glutaraldehyde conjugate with small amounts of deferoxamine-glutaraldehyde-deferoxamine conjugate, unreacted glutaraldehyde, and unreacted deferoxamine.

Human holotransferrin, the iron saturated form of transferrin, was purchased from Sigma Chemical Co., St. Louis, Mo. A volume of 4.5 ml of a 10% solution of transferrin was reacted with an equal volume of the above-prepared solution containing deferoxamine-glutaraldehyde conjugate. A control solution of transferrin mixed with an equal volume of saline was prepared as a control. The concentration of the deferoxamine-glutaraldehyde adduct in the final mixture was 25 mM compared to 5% or 0.62 mM of the protein.

Following a 10 minute incubation, 2.25 ml of 100 mM sodium cyanoborohydride was added to the reaction solution. The control solution was similarly diluted. Following 10 minutes of incubation, both solutions were dialyzed against saline to remove unreacted low molecular weight material.

Following overnight dialysis, the concentration of transferrin was 0.30 in the reaction solution and 0.22 mM in the control solution. These solutions were subsequently diluted to 0.125 mM and, following the addition of excess ferrous sulfate, the absorbance was read at 429 mM to determine the number of bound deferoxamine molecules per transferrin molecule. The following values were obtained:

TABLE 1

| | Absorbance (420 nm) |
|---|---|
| REACTION SOLUTIONS | |
| transferrin-deferoxamine + saline | 0.536 |
| B. transferrin-deferoxamine + ferrous sulfate[1] | 1.790 |
| CONTROL SOLUTIONS | |
| C. control transferrin + saline | 0.499 |
| D. control transferrin + ferrous sulfate[1] | 0.604 |

[1]The final concentration of ferrous sulfate in solutions B and D (control) was 10 mM; the absorbance of 10 mM ferrous sulfate at 429 nm is 0.010.

The increase in absorbance of 0.105 units upon addition of ferrous sulfate to the control transferrin solutions (solution D (0.604) minus solution C (0.499)) represents non-specific binding of ferric iron to the protein. The increase in optical density following addition of ferrous sulfate to reaction solution B containing transferrin-deferoxamine conjugate represents binding of ferric iron to deferoxamine. Solution A containing transferrin-deferoxamine conjugate alone had an optical density of 0.536. In solution B, the addition of ferric sulfate to the conjugate showed an optical density of 1.790, or an increase of 1.254 (solution B (1.790) minus control solution A (0.536)). The optical density resulting from non-specific binding of ferric iron to transferrin protein (solutions D minus C, or 0.105) is then subtracted from the 1.254 figure to indicate a net increase in optical density of 1.149 for the transferrin-deferoxamine-ferrous sulfate solution B.

Since the millimolar extinction coefficient of deferoxamine is 2.3, the observed value corresponds to 0.5 mM deferoxamine. The concentration of transferrin protein in the control and reaction solution was 0.125 mM. Therefore, each transferrin molecule carries, on the average, four bound deferoxamine molecules.

To determine whether the observed change in absorbance of solution B represents bound deferoxamine, the material in solution B was precipitated with trichloroacetic acid. The supernatant was then neutralized and the optical density measured at 429 nm. This control experiment revealed that less than 10% of the deferoxamine remained in the supernatant. Therefore, more than 90% of the deferoxamine was bound to the protein.

Following calculation of the concentration of bound deferoxamine, larger quantities of the transferrin-deferoxamine-ferric iron adduct may be prepared by adding calculated quantities of an iron salt, such as ferric ammonium sulfate to the transferrin-deferoxamine solution. Following diafiltration against normal saline, the preparation is sterile filtered, and either lyophilized or used directly as a 5% solution.

By altering the ratio of deferoxamine-glutaraldehyde to protein, as many as 10 moles of deferoxamine may be added per mole of protein. However, such preparations show a significant amount of cross-linked protein when analyzed by polyacrylamide gel electrophoresis. Preferably the ratio of deferoxamine to protein is about 4-6 moles deferoxamine:1 mole protein.

The transferrin-deferoxamine-ferric deferoxamine iron adduct is also capable of unaltered affinity for binding to human transferrin receptor on HeLa cells. The retention of specific receptor binding affinity which may be characteristic of the unaltered protein component by the modified protein-deferoxamine conjugate is an important parameter for achieving binding and the subsequent image enhancement of those cells and tissues containing high concentrations of the transferrin receptor. Accordingly, it is preferred that the adduct of the invention retain the receptor binding affinity of its protein moiety.

EXAMPLE III

Magnetic Relaxivity Properties of the Hydroxyethyl Starch-deferoxamine-ferric Iron Adduct Studies of the relaxivity of deferoxamine-ferric iron complex, or ferrioxamine, has been carried out by several investigators. Studies indicate that the millimolar relaxivity of this metal complex is somewhat below 1.0 $s^{(-1)}$. A value of 1.37 $s^{(-1)}$ at 20 MHz has been reported by Wesbey, et al. and Worah, et al. (1984). A lower value of 0.9 $s^{(-1)}$ at 50 MHz has also been reported and likely corresponds to a value of 1.0-1.1 at 20 MHz. A value of 1.8 at 20 MHz has also been reported. Studies suggest a doubling of the millimolar relaxivity of hydroxyethyl starch (HES) bound deferoxamine-ferric iron to a millimolar value of near 2.0. This suggestion is consistent with an expected slowing of the rotational freedom of the bound chelator. A value of 1.6 $s^{(-1)}$ at 20 MHz for an HES-deferoxamine-ferric iron conjugate was obtained.

EXAMPLE IV

Hemodynamic Effects and Influence on Ischemic Insult Following Infusion of the Hydroxyethyl Starch-deferoxamine-ferric Iron Adduct in the Dog A model was designed in which three forms of deferoxamine were tested according to their influence on myocardial function secondary to an ischemic insult. In this model of the "stunned myocardium," a defined region of the heart, was exposed to short term ischemic insults. These ischemic insults correspond to myocardial injury that can be sustained following angioplasty and other like cardiac procedures.

The effect on myocardial function was determined using deferoxamine (DFO), a conjugate of deferoxamine attached to a low molecular weight form of hydroxyethyl starch (HES-DFO), and a hydroxyethyl starch-deferoxamine conjugate (HES-DFO) in which 90-95% of the iron sites had been saturated with ferric iron. The physiological effects of HES-DFO-ferric iron in relation to DFO and HES-DFO were studied to determine the suitability of the hydroxyethyl starch-deferoxamine-ferric iron adduct as an MR image contrast agent.

It has been demonstrated that both deferoxamine and HES-deferoxamine protect ischemic tissue against oxygen radical mediated injury occurring secondary to ischemia and reperfusion (Bolli, et al, *Am. J. Physiol.: Heart Circ. Physiol.* 22: H1372-H1380 (1987); Farber, et al., *Circ. Res.* 63: 351-360 (1988)). An MR contrast agent preferably neither improves nor worsens such injury, but simply enhances the quality of the MR image. Similarly, it has been shown that both deferoxamine and ferrioxamine are associated with significant toxicity when administered intravenously. This toxicity may manifest itself by hypotension which is occasionally severe. A preferred MR imaging enhancer does not cause adverse hemodynamic effects even when administered into the vascular compartment in high concentrations.

Procedure

The physiological properties of deferoxamine HES-deferoxamine conjugate, and HES-deferoxamine-ferric iron adduct were characterized and compared in a canine model of the stunned myocardium.

Adult male and female mongrel dogs were anesthetized and ventilated at 10-15 breaths/minute with a tidal volume of 15 ml/kg by a Harvard respirator. Atelectasis was prevented by maintaining an end expiratory pressure of 5-7 cm of water with a trap. Body temperature was maintained at 38° C. with a heating pad. Throughout the experiment pH, $pO_2$ and $pCO_2$ were maintained at physiological levels by adjusting the respiratory rate and volume, and by infusing sodium bicarbonate and supplemental 100% oxygen.

Aortic blood pressure and left ventricular pressure were monitored by inserting a double pressure transducer-tipped catheter into the aorta and left ventricle via the carotid artery. Left ventricular dP/dt was determined by electronic differentiation of the left ventricular pressure pulse.

The left jugular vein was cannulated for the administration of deferoxamine (DFO), hydroxyethyl starch-deferoxamine conjugate (HES-DFO) and hydroxyethyl starch-deferoxamine-ferric iron adduct (HES-DFO-ferric iron).

A left thoracotomy was performed at the fifth intercostal space, the pericardium incised and the heart suspended in a cradle. A portion of the left anterior descending coronary artery (LAD) was isolated distal to the first diagonal branch and a electromagnetic flow probe was placed around the vessel. LAD blood flow was measured with a flow meter. Distal to the flow probe, a micrometer driven mechanical occluder was placed to produce a total occlusion of the LAD and to subsequently allow reperfusion. The heart was paced at 150 beats/min.

Myocardial segment function, expressed as percent segment shortening, or % SS, as a measure of altered myocardial function following ischemia/reperfusion, was measured in the regions perfused by the LAD and the left circumflex coronary artery by using two sets of piezoelectric crystals. The precalibrated crystals were inserted into the subendocardium. The leads of each crystals were connected to an ultrasonic amplifier which transformed the sound pulse transmitted between the two crystals into an electrical signal proportional to the distance between them. These tracings were monitored with an oscilloscope. The % SS was calculated according to the following equation:

$$\% SS = (DL - SL)/DL \times 100$$

where DL is the diastolic segment length, and SL is the systolic segment length.

Regional myocardial blood flow was determined by the use of the microsphere technique. The left atrial appendage and the right femoral artery were cannulated for the administration of microspheres and for the withdrawal of a reference blood flow sample, respectively. Radioactive microspheres (15±3 μm diameter) were injected into the left atrium followed by a 6 ml saline wash. Before administration of the microspheres, a reference blood flow sample was withdrawn from the femoral artery at a constant rate for 2-3 minutes.

At the completion of each experiment, India ink was injected into the LAD at the point of the flow probe at aortic perfusion pressure to delineate the ischemic bed size. Subsequently, the heart was removed and stored overnight in 10% formalin. The following day, the heart was sectioned into subepicardium, midmyocardium and subendocardium of both normal and ischemic regions and the samples weighed. The radioactivity in each tissue sample was counted in a gamma counter. Using measured reference blood flow determinations, both myocardial and transmural blood flows were calculated.

Blood levels of DFO, HES-DFO and HES-DFO-ferric iron were obtained before, during and after coronary occlusion in blood samples obtained from the femoral artery. Blood samples were centrifuged and plasma samples stored at −70° C. for later analysis. The methodology for these measurements are described in Hallaway, et al., *Proc. Nat. Acad. Sci. USA*, 86: 10108-10112 (1989), the disclosures of which are incorporated by reference herein.

After surgical preparation and stabilization, control measurements of hemodynamics were obtained and radioactive microspheres administered to determine regional myocardial blood flow. Four groups of dogs were used. One group received saline, the other groups received 50 mg/kg of deferoxamine or deferoxamine-ferric iron (ferrioxamine) equivalents at 30 minutes prior to and during the 15 minute period of occlusion. The solutions were infused at a rate of 2.3 ml/min. At the end, the occluder was released slowly and the LAD reperfused for three hours. Hemodynamics were continuously recorded during this period. Radioactive microspheres were infused at 12 minutes of occlusion and at 30 and 180 minutes of reperfusion.

Solutions contained 10% HES-DFO or 10% HES-DFO-ferric iron in physiological saline. The molecular weight of the preparation used in this study was 20,000 with a vascular half-life of approximately 2 hours. The chelator content of the HES-DFO conjugate and HES-DFO-ferric iron adduct was approximately 15% (w/w). The concentration of deferoxamine and deferoxamine-ferric iron (ferrioxamine) in these preparations was 28 mM. HES-DFO-ferric iron was prepared by addition of 0.95 equivalents of ferric iron as ferric chloride, based on the measured content of available iron building sites, to a solution containing HES-DFO. The resulting acidic solution was neutralized with sodium hydroxide and filtered before use.

Results

Following exclusion of animals for technical reasons or for death due to ventricular fibrillation, 27 animals were included in the study. Analysis of data was carried out in nine control dogs, seven dogs treated with HES-deferoxamine conjugate, five dogs treated with the HES-deferoxamine-ferric iron adduct, and six dogs treated with deferoxamine alone as a control. The size of the left ventricle and the area at risk were similar among the animals used in the study so that, among the four groups, equivalent perfusion bed areas were subjected to ischemia.

1. Hemodynamics.

No differences in basal and paced heart rate were observed in the animal subjects. Further, no differences were observed between the control (DFO), HES-DFO and HES-DFO-ferric iron groups during the experiment. These results indicate that the HES-DFO-ferric iron adduct does not cause changes in hemodynamic stability. Within the DFO group of animals, however, a significant decrease in mean arterial pressure during drug infusion was observed. Thus, even though DFO was delivered slowly and in a controlled fashion, it caused significant hypotension.

No differences in regional myocardial blood flow between the four groups prior to ischemia, during occlusion and during reperfusion were observed. Therefore, the HES-DFO-ferric iron adduct did not influence coronary blood flow in the normal and in the compromised heart. 2. Myocardial Function Myocardial segment function is expressed as present segment shortening, or % SS. No differences in the subendocardial wall function in the non-ischemic (LCX) area was observed in the four groups. In the ischemic LAD region, there was a similar reduction in % SS in all four groups which is an indication of passive systolic lengthening.

During reperfusion, the recovery of % SS was similar in the saline and the HES deferoxamine-ferric iron treated animals. This indicates that the HES deferoxamine-ferric iron adduct neither protects against nor further aggravate injury caused during ischemia. These results contrast with those of HES-deferoxamine treated animals in which % SS was significantly improved as compared to the saline and HES deferoxamine-ferric iron treated animals, as illustrated in FIG. 1. This suggests that the iron chelating capacity of HES-deferoxamine attenuates the injury caused by ischemia and reperfusion. In addition, no residual colloid protective effect of the HES-DFO-ferric iron adduct was observed. Therefore, the protective effect of HES-DFO can be assigned to the iron chelating properties of the HES-DFO conjugate.

3. Plasma Levels of Chelator Conjugates

Figure 2:
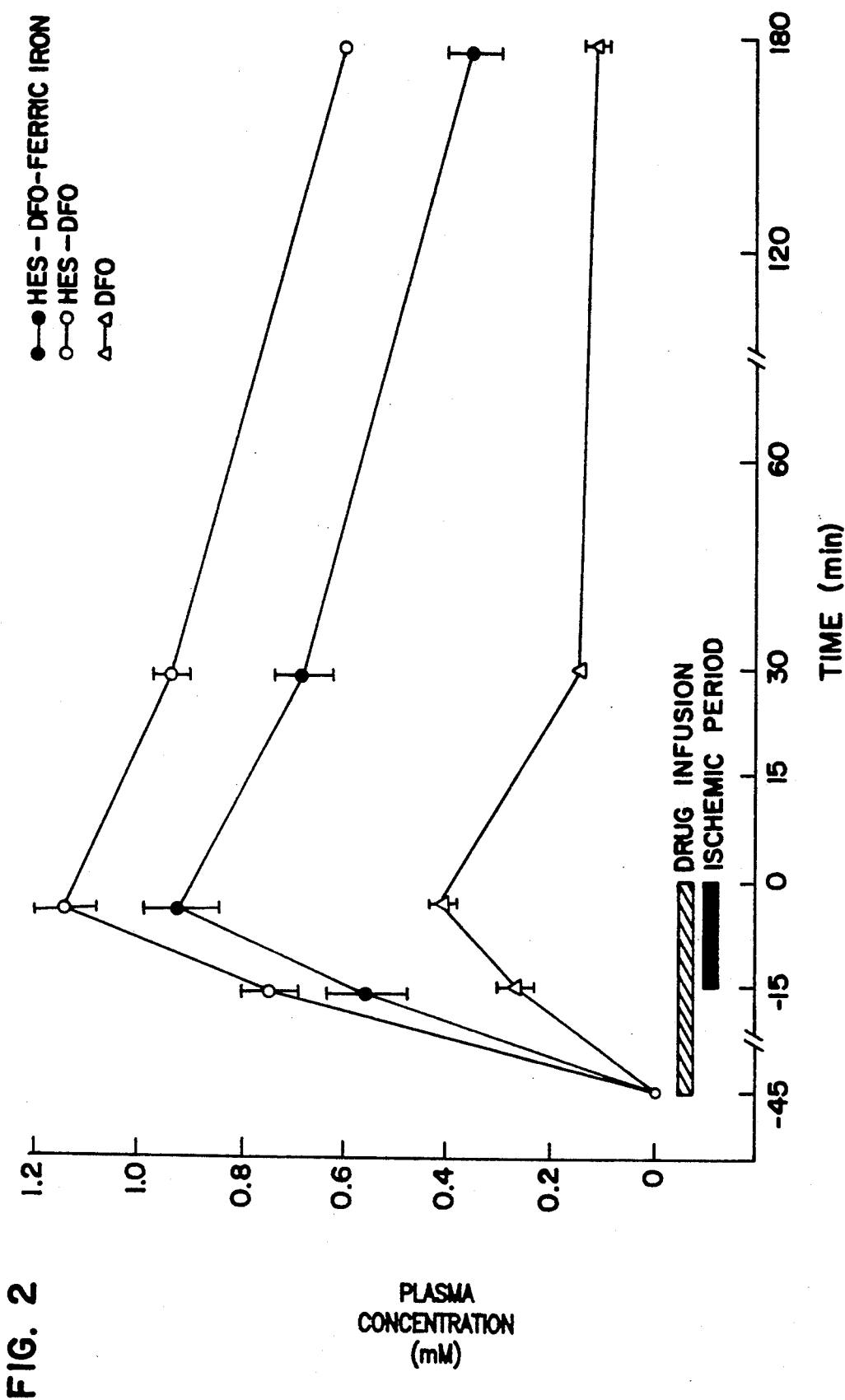
FIG. 2 illustrates the plasma concentration of HES-DFO (open circles, n=7), HES-DFO-FERRIC IRON (filled circles, n=4) and DFO (open triangles, n=6) prior to LAD occlusion, during occlusion and at various times following reperfusion. The hatched and closed bars indicate the period of drug infusion and LAD occlusion, respectively. All values are the mean ±SEM. * $p<0.05$ vs DFO group.

The plasma levels of DFO, HES-DFO and HES-DFO-ferric iron are illustrated in FIG. 2. The infusion of 50 mg/kg of HES-DFO or HES-DFO-ferric iron over 45 minutes yielded a plasma concentration of approximately 1.0 mM. The maximal plasma concentration of DFO reached about 0.4 mM and then rapidly decreased.

Summary

In sum, the hydroxyethyl starch-deferoxamine-ferric ferric iron adduct did not cause any observable toxicity when infused intravenously at a dose equivalent to 50 mg/kg deferoxamine-ferric iron (ferrioxamine). The effect of the HES-deferoxamine-ferric iron adduct on myocardial function is indistinguishable from that of a similar volume of saline, indicating that there is neither a protective nor adverse effect on the heart. Plasma concentrations in the millimolar range were maintained over a 30 minute period following the termination of infusion of the adduct.

What is claimed is:

1. A method for magnetic resonance imaging of a body system of a mammal, comprising:
   a) administering a diagnostically effective amount of a contrast agent to a mammal such that the contrast agent is distributed to the body system, said agent comprising a pharmaceutically-acceptable contrast agent having a molecular weight of about 5,000 to 250,000 daltons, as determined by gel permeation chromatography, and being formed of a conjugate of a least one deferoxamine moiety covalently bonded to a polymer, and ferric iron chelated to the deferoxamine moiety; whereby when the contrast agent is administered to the mammal by intravenous injection, the molecular weight of the contrast agent is effective to retain the contrast agent within the vascular compartment of the body system for a time effective to enhance the magnetic resonance imaging of the body system; and b) determining the magnetic image of the system or a portion thereof by magnetic resonance imaging.

2. The method according to claim 1 wherein a feature within the vascular system is enhanced.

3. The method according to claim 1 wherein the agent is administered intravenously.

4. A method for magnetic resonance imaging of a body system of a mammal, comprising:

a) administering to a mammal by an oral, vaginal or rectal route, a diagnostically effective amount of a contrast agent such that the contrast agent is distributed to the gastrointestinal body system of the mammal; said agent comprising a pharmaceutically-acceptable contrast agent having a molecular weight of about 5000 to 250,000 daltons, as determined by gel permeation chromatography, and being formed of a conjugate of at least one deferoxamine moiety covalently bonded to a polymer, and ferric iron chelated to the deferoxamine moiety; whereby the molecular weight of the contrast agent is effective to retain the contrast agent within the gastrointestinal body system for a time effective to enhance the magnetic resonance imaging of the body system; and b) determining the magnetic image of the body system or a portion thereof by magnetic resonance imaging.

5. The method according to claim 1 wherein the agent is admininstered by direct injection into the system.

6. The method according to claim 4 wherein the agent is administered orally or rectally.

7. The method according to claim 1, wherein the polymer is protein serum albumin or transferrin.

8. The method according to claim 1, wherein the polymer is dextran, starch, hyaluronic acid, cellulose or inulin.

9. The method according to claim 1, wherein the contrast agent has a molecular weight of about 10,000 to 50,000 Daltons, as determined by gel permeation chromatography.

10. The method according to claim 4, wherein the polymer is cellulose or agarose.

* * * * *

UNITED STATES PATENT AND TRADEMARK OFFICE
CERTIFICATE OF CORRECTION

PATENT NO. : 5,268,165

DATED : December 7, 1993

INVENTOR(S) : Bo E. Hedlund et al.

It is certified that error appears in the above-identified patent and that said Letters Patent is hereby corrected as shown below:

At column 12, line 47, for "Hydroxyethvl" read --Hydroxyethyl--.

At column 13, lines 48-49, for "glutaralehyde" read --glutaraldehyde--.

At column 14, in Table 1 (first entry) at line 18, before "transferrin" insert --A.--.

At column 19, line 3, for "a" read --at--.

Signed and Sealed this

Twelfth Day of July, 1994

Attest:

BRUCE LEHMAN

Attesting Officer   Commissioner of Patents and Trademarks